United States Patent
Piety et al.

(10) Patent No.: US 6,234,021 B1
(45) Date of Patent: May 22, 2001

(54) ENHANCED DETECTION OF VIBRATION

(75) Inventors: Kenneth R. Piety; James C. Robinson; William S. Johnson, all of Knoxville; James Brent Vanvoorhis, Kingston, all of TN (US)

(73) Assignee: CSI Technology, Inc., Wilmington, DE (US)

(*) Notice: Subject to any disclaimer, the term of this patent is extended or adjusted under 35 U.S.C. 154(b) by 0 days.

(21) Appl. No.: 09/243,324

(22) Filed: Feb. 2, 1999

(51) Int. Cl.[7] .......................... G01H 17/00; G01N 29/12; G01N 29/14

(52) U.S. Cl. .................. 73/592; 73/593; 73/660; 73/661

(58) Field of Search ............................ 73/661, 660, 659, 73/658, 649, 593, 592, 587

(56) References Cited

U.S. PATENT DOCUMENTS

| | | | |
|---|---|---|---|
| 2,753,948 | * 7/1956 | Ongaro | 73/661 |
| 3,089,333 | * 5/1963 | Kleesattel | 73/661 |
| 3,365,935 | * 1/1968 | Kane | 73/661 |
| 3,675,053 | 7/1972 | Mifune et al. | 310/8.2 |
| 4,038,866 | * 8/1977 | Johnson | 73/661 |
| 4,041,775 | 8/1977 | McNamee | 73/70.2 |
| 4,408,285 | * 10/1983 | Sisson et al. | 73/602 |
| 4,520,674 | 6/1985 | Canada et al. | 73/660 |
| 4,562,740 | 1/1986 | Webber et al. | 73/651 |
| 4,612,620 | * 9/1986 | Davis et al. | 73/660 |
| 4,655,082 | 4/1987 | Peterson | 73/594 |
| 4,755,953 | 7/1988 | Geithman et al. | 364/507 |
| 4,771,637 | 9/1988 | Kubler | 73/493 |
| 4,823,600 | * 4/1989 | Biegel et al. | 73/592 |
| 4,827,771 | 5/1989 | Cary et al. | 73/644 |
| 5,058,434 | * 10/1991 | Zaschel | 73/659 |
| 5,103,675 | 4/1992 | Komninos | 73/592 |
| 5,379,643 | 1/1995 | Taylor | 73/654 |
| 5,381,692 | * 1/1995 | Winslow et al. | 73/593 |
| 5,557,969 | 9/1996 | Jordan | 73/592 |
| 5,697,450 | 12/1997 | Stehling et al. | 169/65 |
| 5,955,670 | * 9/1999 | Goodman et al. | 73/592 |
| 6,079,275 | * 6/2000 | Komninos | 73/661 |

* cited by examiner

Primary Examiner—Daniel S. Larkin
Assistant Examiner—Rose M. Miller
(74) Attorney, Agent, or Firm—Luedeka, Neely & Graham, P.C.

(57) ABSTRACT

A device detects an emission source of a vibration signal against a background of noise, where the vibration signal is produced by a mechanical system and has one or more frequency components. A sensor senses the vibration signal and produces a sensor signal corresponding to the vibration signal. The sensor has a mechanical frequency selection structure for mechanically resonating at desired frequencies and for mechanically attenuating a frequency component of the vibration signal having a frequency outside the desired frequencies. The mechanical frequency selection structure thus produces a mechanically-tuned sensor signal. Electrical frequency selection filters electrically attenuate a frequency component of the mechanically-tuned sensor signal having a frequency outside the desired frequencies. The electrical frequency selection filters thus produce an electrically-tuned sensor signal. The device has at least one amplifier with gain for producing an amplified signal corresponding to the electrically-tuned sensor signal. An amplitude characteristic determination circuit determines an amplitude characteristic corresponding to the vibration signal's amplitude. The amplitude characteristic determination circuit also generates an amplitude indication based on the amplitude characteristic. The amplitude indication and adjusts the gain of the amplifier based at least in part on the amplitude indication.

16 Claims, 9 Drawing Sheets

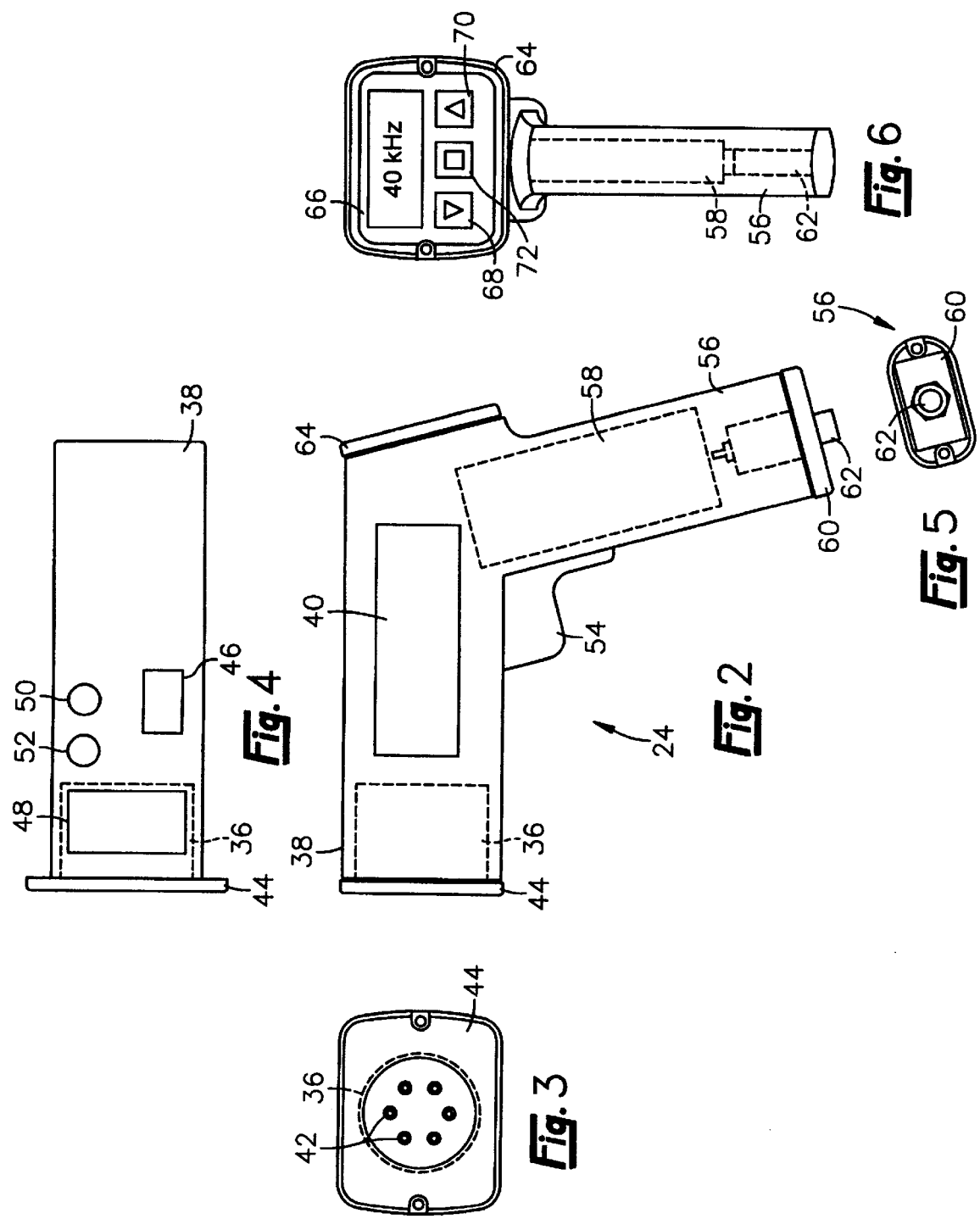

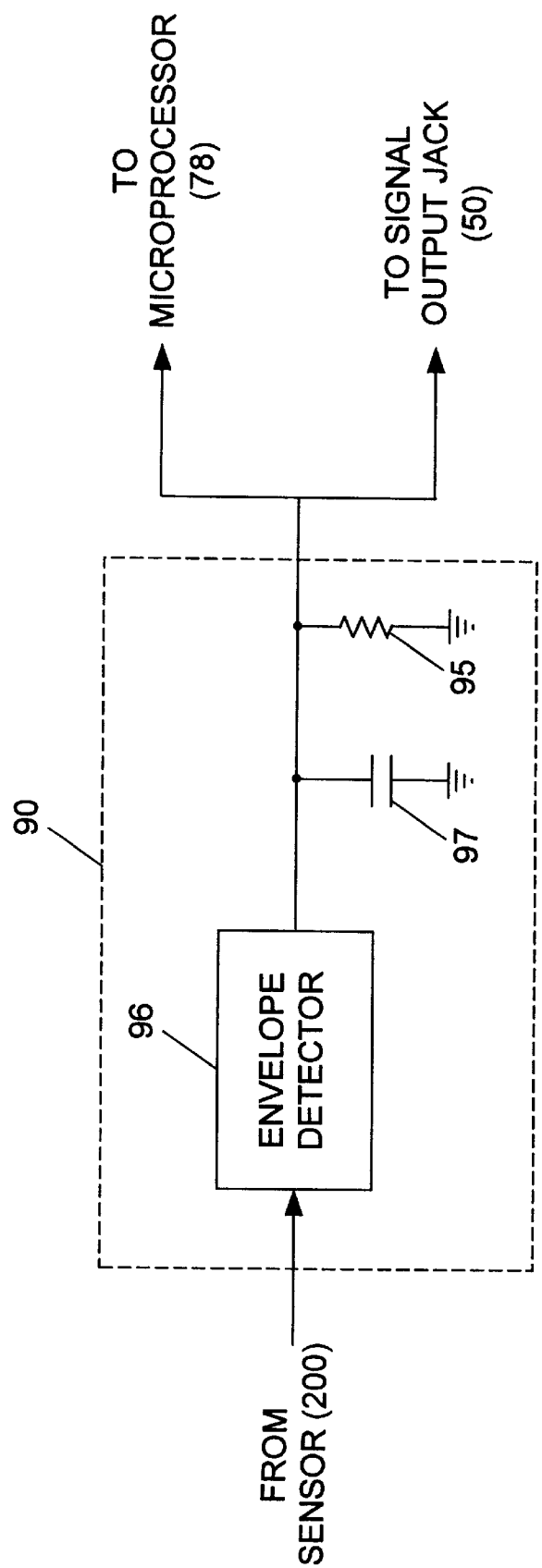

ENHANCED DETECTION OF VIBRATION

TECHNICAL FIELD

The present invention is generally directed to the detection and monitoring of sound and vibration signals. The invention is more particularly directed to autoranging of sonic and ultrasonic signals in selected frequency bands to provide for enhanced audible detection and monitoring capabilities.

BACKGROUND OF THE INVENTION

The normal frequency range for human hearing is roughly 20 to 20,000 Hz. Vibration signals having frequencies of above about 20,000 Hz are in the ultrasonic range. Many industrial processes, including almost all sources of friction, create some ultrasonic vibrational noise. For example, leaks in pipes, machinery defects, and electrical arcing produce ultrasonic signals having frequencies too high for the human ear to detect.

In the past, ultrasonic sensors have been used in industrial settings to sense these ultrasonic signals and to detect abnormally high levels of ultrasonic sound which may indicate a mechanical fault in a machine. To monitor the ultrasonic signals produced by operating machinery, an operator would use an ultrasonic sensor to obtain a reading indicating the strength of the ultrasonic signals near the machine. If the ultrasonic signal levels generated by one machine were abnormally large, the operator would investigate further to determine if a problem existed with the noisy machine. If the ultrasonic signal levels were approximately equal to those produced by a properly functioning machine, the operator would assume the machine was properly functioning and simply proceed to the next machine.

Since ultrasonic signals generally cannot be heard by the human ear, ultrasonic sensing devices typically incorporate a heterodyne circuit to generate an audio signal that is a lower-frequency representation of the ultrasonic signal. The typical ultrasonic sensing device includes headphones or earphones to present the audio signal, which has a frequency within the range of human hearing, to the operator. Thus, when the ultrasonic sensing device detects an ultrasonic signal, the operator can hear an audio representation of the ultrasonic signal in the headphones.

As discussed above, machine elements such as bearings, valves, and gears, even those operating normally, produce vibration signals at both audible and ultrasonic frequencies. When trying to detect a machine fault using an ultrasonic sensing device, an operator listens for an abnormal signal, such as an impact sound, against a background of noise produced by the machinery. (For the purposes of this description, the term "background noise" is understood to include the noise that is present even in the absence of a fault condition, such as the noise generated by the normal operation of the machinery.) Many machine faults can be classified as impacts. For example, a bearing with a chip in a race, or a cracked gear tooth will produce an impact signal of only a few milliseconds or less in duration. The severity of the fault, the load conditions of the machine, as well as the amplitude of the normal background noise will determine the signal to noise ratio of the impact signal versus the background noise.

Given the noisy industrial environment and the brief, often transitory, nature of many fault signals that an operator is trying to hear, many important fault signals are not heard. To maximize the utility of the detector, it should be optimized to enhance the ability of the user to detect fault signals.

SUMMARY OF THE INVENTION

In the present invention, a preferred detector of vibration is optimized to enhance user detection of signals by mechanical and electrical tuning and amplitude autoranging. Mechanical and electrical tuning help the user to focus on vibration frequencies of interest, those that contain useful information in a particular situation. Amplitude autoranging guards against a common problem of manually adjusting the gain too high in an effort to hear better, only to defeat the ability to hear short duration impacts at all. If the gain is too high, the user may think he is hearing well, when in fact, the amplifier gain is adjusted so high that the impact signals are beyond clipping, and the background noise has been amplified to such a degree that the impact signals are acoustically masked. When this occurs, the impact signals may go unnoticed by the user.

The present invention addresses these and other problems by providing a device for detecting an emission source of a dynamic signal against a background of noise, where the vibration signal is a dynamic pressure or vibration signal produced by a machine or other mechanical system under test and has one or more frequency components. A sensor senses the dynamic signal and produces a sensor signal corresponding to the dynamic signal. The sensor has mechanical frequency selection means for mechanically resonating at desired frequencies and for mechanically attenuating frequency components of the dynamic signal having frequencies outside the desired frequencies. The mechanical frequency selection means thus produce mechanically-tuned sensor signals. Electrical frequency selection means electrically attenuate frequency components of the mechanically-tuned sensor signal having frequencies outside the desired frequencies. The electrical frequency selection means thus produce an electrically-tuned sensor signal.

The device has at least one amplifier with gain for producing an amplified signal corresponding to the electrically-tuned sensor signal. Amplitude characteristic determination means determine an amplitude characteristic corresponding to the dynamic signal's amplitude. The amplitude characteristic determination means also generate an amplitude indication based on the amplitude characteristic. Automatic gain adjustment means receive the amplitude indication and adjust the gain of the amplifier based at least in part on the amplitude indication.

In preferred embodiments of the invention, the mechanical frequency selection means include a resonator that contacts the machine or mechanical system being tested and vibrates at particular resonant frequencies in response to a vibration signal. A transducer, which is in contact with the resonator, produces electrical signals corresponding to the resonant frequencies of the resonator. A magnetic mount, which is designed to be integral with the resonator, contacts the mechanical system and holds the resonator in contact with the mechanical system.

The electrical frequency selection means of some embodiments incorporate frequency switching means that enable a user of the device to choose one of several selected frequency components of the sensor signal. Based upon the selected frequency component, the electrical frequency selection means produce a frequency selection indication. Filter selection means receive the frequency selection indication and select one of several filters based on the frequency selection indication. Each of these filters is tuned to one of the selected frequency components, such that the selected filter receives the mechanically-tuned sensor signal and electrically attenuates frequencies other than one of the selected frequency components to which the filter is tuned.

Thus, the present invention enhances the detectability of vibration signals by adjusting the frequency and the amplitude of the vibration signals to ranges that are optimum for detection under the particular circumstances.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows:

FIG. 2 is a side view of the gun-shaped housing showing the locations of the main internal components of the ultrasonic monitoring device;

FIG. 3 is a front view of the housing showing the bottom of the sensor socket;

FIG. 4 is a bottom view of the barrel of the housing showing the location of the input and output ports;

FIG. 5 is a bottom view of the grip of the housing showing the headphone jack;

FIG. 6 is a rear view of the housing showing the display and user input keys;

FIG. 11 is a block diagram of an embodiment of a received signal strength indicator.

DETAILED DESCRIPTION OF THE PREFERRED EMBODIMENT

The monitoring device of the present invention effectively locates leaks of air, steam, or other gases from pressurized systems as well as arching and electrical corona, which may produce sonic and ultrasonic signals. Furthermore, the monitoring device can diagnose and analyze steam trap operation, bearing and gear defects, cavitation and surging in pumps and compressors, lubrication problems in dynamic equipment, valve operation, steam lines, and piston friction and detonation problems in reciprocating equipment. Thus, the invention is used to detect vibration signals, including sonic and ultrasonic sound waves propagating through the air and sonic and ultrasonic vibrations in a mechanical system.

Figure 1:
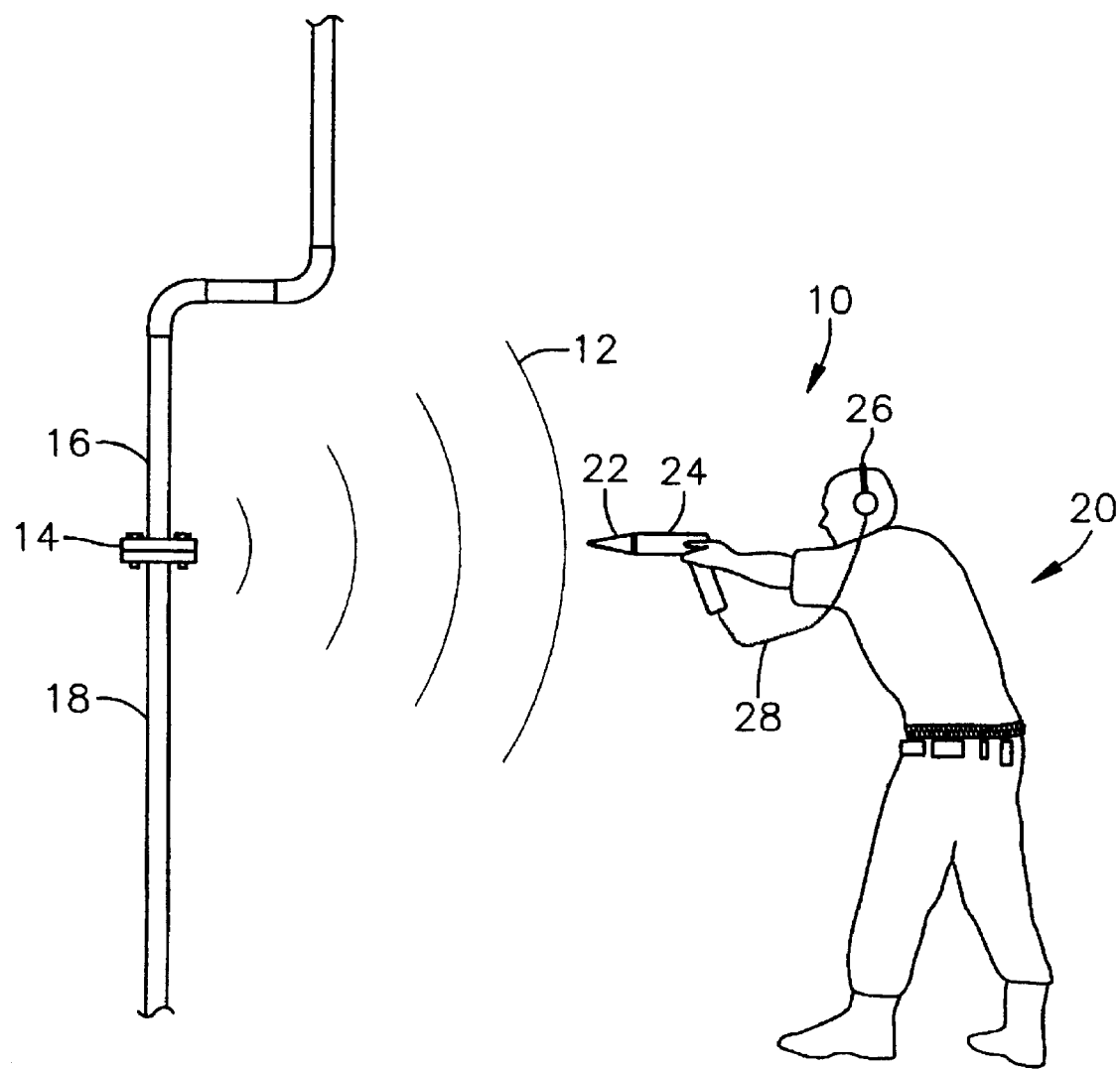
FIG. 1 is a perspective view of an operator using the ultrasonic monitoring device of the present invention.

FIG. 1 shows a preferred embodiment of a monitoring device 10 for detecting and monitoring ultrasonic pressure signals 12 emanating as pressure waves from the intersection 14 of two abutting pipes 16 and 18. In the case of leak detection, as illustrated in FIG. 1, the monitoring device 10 is principally used by the operator 20 to determine the location from which the ultrasonic pressure signals 12 are emanating. The embodiment of the monitoring device 10 shown in FIG. 1 includes an airborne sensor head 22 mounted at the end of the barrel of a portable gun-shaped housing 24. In operation, the housing 24 is held by the operator 20 and pointed toward a machine or device that might have a leak or defect that is radiating ultrasonic pressure signals 12. The operator 20 wears headphones 26 that are attached to the housing 24 via a cord 28. The headphones 26 produce audible audio signals, the volume of which indicates the relative strength of the ultrasonic pressure signals 12 received by an ultrasonic pressure sensor within the sensor head 22.

In the preferred embodiment, the sensor head 22 is directional. Thus, when the sensor head 22 is pointed away from the source 14 of the ultrasonic pressure signals 12, the strength of the ultrasonic pressure signals 12 detected by the sensor within the sensor head 22 decreases. When the sensor head 22 is pointed toward the source 14 of the ultrasonic pressure signals 12, the strength of the ultrasonic pressure signals 12 detected by the sensor within the sensor head 22 increases.

The increase and decrease in the strength of the detected ultrasonic pressure signals 12 can be audibly represented in a variety of ways. For example, a rise in the volume of a tone produced by the monitoring device 10 could indicate that the amplitude of the detected ultrasonic pressure signals 12 is growing stronger, while a decrease in the volume of the tone could indicate that the ultrasonic pressure signals 12 are growing weaker. A rise and fall in the pitch of the tone could also indicate a respective rise and fall in the strength of the detected ultrasonic pressure signals 12. Alternatively, a clicking sound, similar to that produced by a Geiger counter, would also serve the function of indicating the strength of the detected ultrasonic pressure signals 12 to the operator 20.

In the preferred embodiment, the ultrasonic pressure signals 12 received by the sensor head 22 are heterodyned to produce related audio signals having frequencies in the audible range. The related audio signals have many of the distinctive properties of the ultrasonic pressure signals 12 from which they were produced. The headphones 26 generate sound based on the audio signals. By listening to the distinctive noise signatures created by different types of ultrasonic signal sources, the operator 20 may be able to identify the type of noise source that is generating the ultrasonic pressure signals 12.

A variety of sensors can be used with the monitoring device 10 depending upon the type of monitoring to be performed. These sensors include airborne sensors that receive pressure signals that propagate through the air (as shown in FIG. 1), as well as contact sensors that receive vibration signals by contacting the vibrating mechanism. Each of these types of sensors are discussed in more detail hereinafter.

While it is appreciated that there are numerous applications for a monitoring device 10, machinery monitoring and leak detection are the primary uses for the monitoring device 10 of the present invention. The frequency range of interest for these applications is approximately 2 to 200 kHz.

It should be understood that vibration or pressure signals produced by most machinery defects or leaks typically do not consist of a single tone or pitch. These signals are broadband, consisting of components having many different frequencies. Based on the complex nature of such signals, an experienced operator can distinguish between the heterodyned ultrasonic sounds produced by different conditions. For example, leaks in pressurized containers generally create a rushing sound, while arcing and electrical corona typically produce a crackling or buzzing sound.

With the exception of the sensor head 22, the headphones 26, and the cord 28, the gun-shaped housing 24 contains most of the components needed to implement the monitoring device 10 in accordance with the present invention. FIG. 2 shows the preferred internal location of the components in the housing 24. A sensor socket 36, located in the barrel 38 of the housing 24, is designed to receive a variety of different sensor heads. When a sensor head is installed in the sensor socket 36, the sensor socket 36 provides electrical contact between the installed sensor head and a set of circuit boards 40 located in the barrel 38 of the housing 24.

As shown in FIG. 3, the electrical connection between a sensor head and the sensor socket 36 are provided by a series of electrical contacts 42 located in the sensor socket 36. In an especially preferred embodiment, the electrical contacts 42 consist of six spring biased pins 42 that create an electrical connection between the pins 42 and corresponding contact pads 108 located on the base of the sensor head. The sensor socket 36 is surrounded by a plate 44 that covers and protects the front of the barrel 38.

With reference to FIG. 2, the monitoring device 10 communicates with external devices by means of several input and output ports located on the lower portion of the barrel 38. As shown in FIG. 4, an RS 232 port 46 is located on the lower portion of the barrel 38, as well as an infrared communications port 48 located beneath the sensor socket 36. The infrared communications port 48, such as a Model No. TIR1000 manufactured by Texas Instruments, provides the circuit 40 the ability to establish wireless communication with an external device. Additionally, a signal output port 50 is located near the RS 232 port 46 and the infrared communications port 48. As described in greater detail hereinafter, the signal output port 50 provides a signal that is the detected envelope waveform of the ultrasonic sensor signal.

Also shown in FIG. 4 is a battery charger jack 52 that is used to receive a DC voltage source for charging a rechargeable battery 58. A standard adapter having a first end for plugging into a common electrical outlet and a second end for engaging port 52 provides power to the battery charger jack 52.

A trigger 54 for activating the monitoring device 10 is located at the junction of the barrel 38 and the grip 56 of the housing 24. The trigger 54 is electrically connected to the circuit 40, such that when the trigger 54 is pressed, the monitoring device 10 begins making measurements, and when the trigger 54 is released, the device 10 ceases making measurements. Thus, the trigger 54 simply functions as an activation switch, and it is understood that this function could be implemented in other ways.

As shown in FIGS. 2 and 5, a headphone jack 62 located on the bottom portion of the grip 56 extends through the handle plate 60 of the housing 24. The headphone jack 62 provides audio signals to the headphones 26 through the removable cord 28 that is electrically connected to the headphones 26. Alternatively, wireless headphones may be incorporated into the present invention.

FIG. 6 shows a rear face 64 of the housing 24 that contains a display 66 that may be viewed by the operator 20 when measurements are made. The display 66, which is preferably a 2×12 character matrix liquid crystal display (LCD), provides visual data indicators and operational information to the operator 20. A down-arrow user-input key 68, an up-arrow user-input key 70, and a mode user-input key 72 are located below the display 66. The grip 56, the headphone jack 62, and the internal rechargeable power supply 58 are also shown in FIG. 6.

Figure 7:
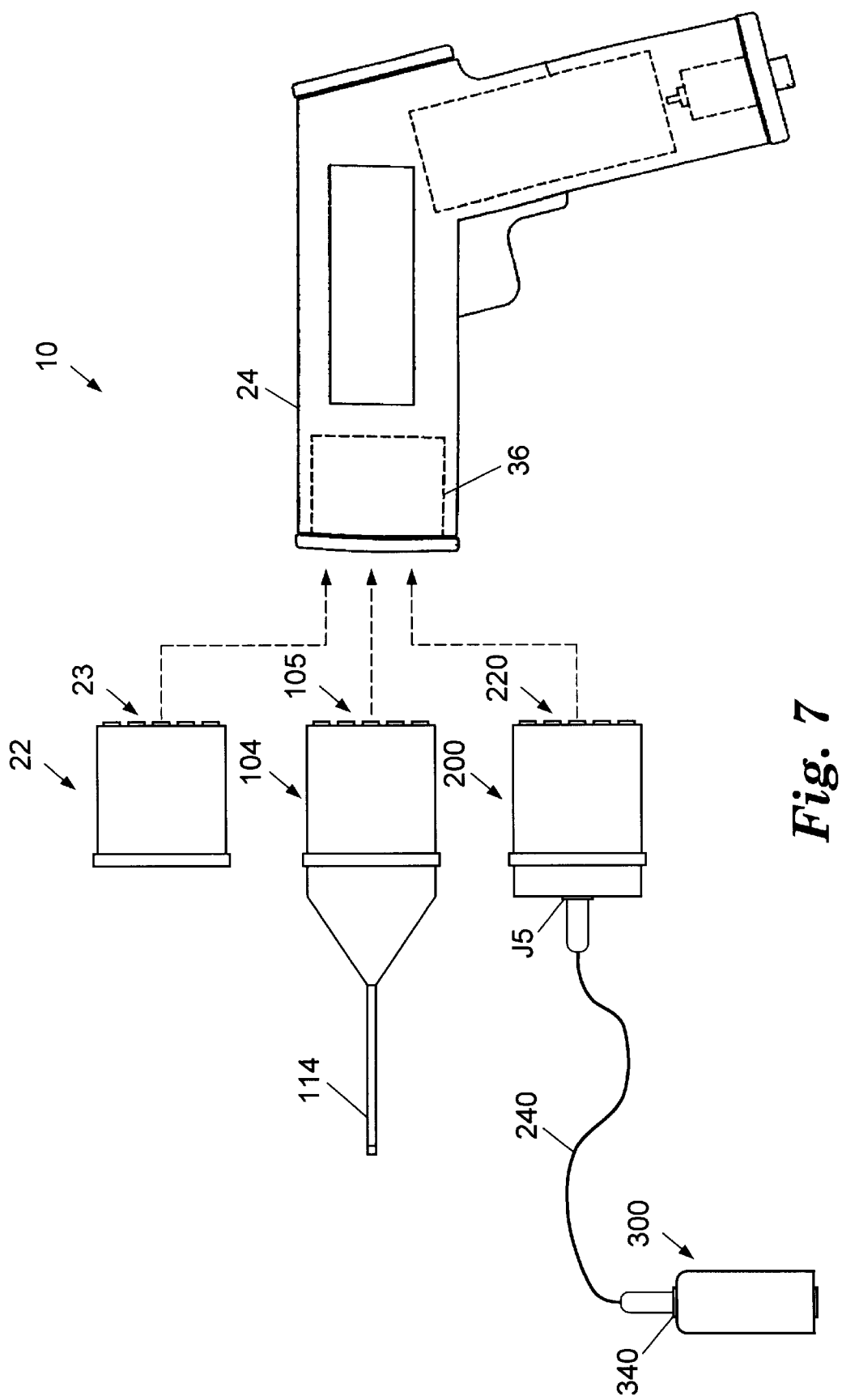
FIG. 7 is a side view of the ultrasonic monitoring device of the present invention with three interchangeable sensor heads.

Shown in FIG. 7 are three different types of sensor heads that may be included in the monitoring device 10. These include the airborne sensor head 22, a tunable contact sensor head 104, and a tunable sensor head 200 that is used in conjunction with a contact sensor, such as a magnetically-mounted resonant sensor 300.

The preferred embodiment of the airborne sensor head 22 utilizes a piezoelectric transducer to produce ultrasonic electrical signals that correspond to the ultrasonic pressure signals 12 reaching the sensor head 22. The airborne sensor head 22 preferably consists of a cylindrical housing with a cylindrical PC board containing contact pads 23 at the base of the housing that serve to establish electrical connections between the sensor head 22 and the sensor socket 36. The piezoelectric transducer is located behind a protective cover in the end of the cylindrical housing opposite the PC board. As discussed in greater detail below, the ultrasonic electrical signals from the piezoelectric transducer are routed to the input of a received signal strength indicator and to the input of a voltage controlled amplifier.

The base of the contact sensor head 104 is similar to the base of the airborne sensor head 22. However, the receiving end of the direct-contact sensor head 104 consists of a long, substantially hollow shaft 114. Vibration signals are received by placing the tip of the hollow shaft 114 of the contact sensor head 104 on the mechanism that is suspected of having a fault. A piezoelectric transducer is attached to the base of the shaft 114 in the sensor head 104. Placing the tip of the shaft 114 against the mechanism producing vibration causes the piezoelectric transducer of the contact sensor head 104 to produce ultrasonic electrical signals. The transducer of the contact sensor head 104 is resonant at several resonant frequencies, such as 4, 28, and 40 kHz. To improve the signal-to-noise ratio around these resonant frequencies, the contact sensor head 104 preferably contains inductive and capacitive band pass resonant filters tuned to these frequencies.

Figure 8:
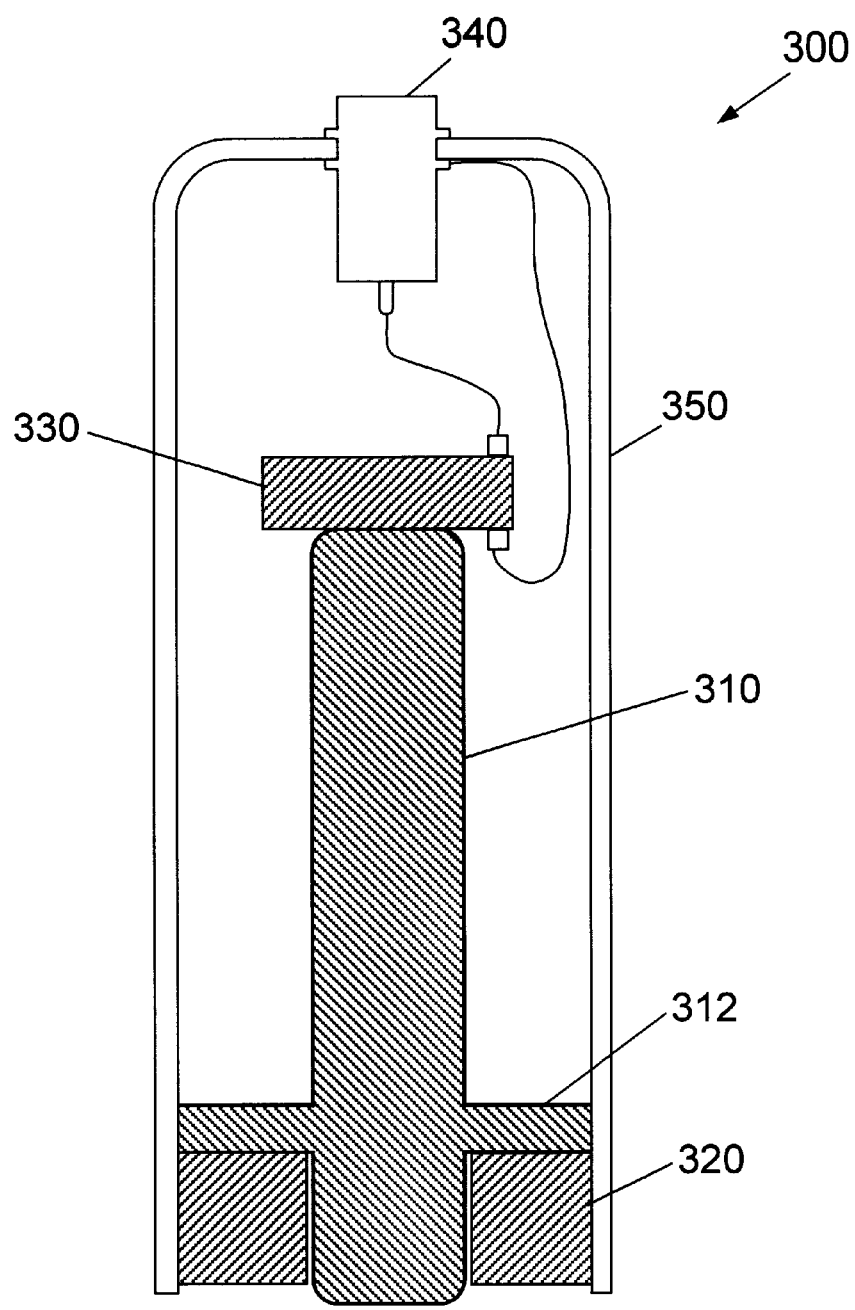
FIG. 8 is a cross-sectional view of an ultrasonic vibration sensor with an integral magnetic mount.

Shown in FIG. 8 is a cross-sectional view of the magnetically-mounted resonant sensor 300. The sensor 300 includes a rod 310 constructed from a particular material, such as low-carbon steel or martensitic stainless steel (magnetic), to a particular length to have resonate nodes at several frequencies of interest. Preferably, the rod is approximately 1.42 inch long and 0.25 inch in diameter. One end of the rod 310 is epoxy-bonded to a piezoceramic transducer 330. The transducer 330 has an intrinsic electro-mechanical resonance which may coincide with, and thus augment, a resonant node frequency of the rod 310. Alternatively, the transducer 330 has an electromechanical resonance that is different from any resonant frequency of the rod 310, thus providing another optimized frequency. In an especially preferred embodiment, the combination of the rod 310 and the transducer 330 provides optimum frequency responses at approximately 4 kHz, 28 kHz, and 40 kHz.

The bottom end of the rod 310 (the end opposite the transducer 330) is held in contact with the mechanism being monitored by a magnetic force provided by a magnet 320. The magnet 320 is an annular disc preferably constructed from a rare earth material, such as Neodymium-Iron-Boron. The poles of the magnet 320 are coincident with its flat top and bottom.

As shown in FIG. 8, integral with the rod 310 is a metal disc 312. Preferably, the disc 312 is machined from the same material as the rod 310, such that the rod 310 and the disc 312 are one continuous piece. The magnetic force of the magnet 320 urges the bottom of the disc 312 to be in contact with the top of the magnet 320. Further, the bottom of the disc 312 is bonded to the top of the magnet 320 by epoxy or other suitable means. When the bottom of the disc 312 is flush with the top of the magnet 320, the bottom end of the rod 310 extends approximately 0.003 inch beyond the bottom surface of the magnet 320. The combination of the steel disc 312 and rod 310 protruding through the magnet 320 completes a flux path of minimum resistance between the poles, and increases the magnetic force of the magnet 320. Thus, when the sensor 300 is put in contact with a metallic mechanism to be monitored, the magnetic force of the magnet 320 holds the bottom end of the rod 310 in constant contact with the surface of the mechanism. This construction makes the sensor 300 substantially self-aligning, and provides for optimum contact between the bottom end of the rod 310 and a variety of surface shapes, including flat, convex, and spherical surfaces. The optimum contact between the rod 310 and the surface of the mechanism being monitored ensures that transmission of vibration from the surface to the transducer 330 is not substantially attenuated.

As the piezoceramic transducer 330 vibrates, it generates an electrical vibration signal that is provided to the connector 340. The connector 340 protrudes through the top of a cover 350 that encloses and protects the transducer 330, rod 310, and magnet 320. Preferably, the cover 350 is constructed from austenitic (nonmagnetic) stainless steel, and is press-fit and epoxy-bonded to the perimeter of the magnet 320.

In the preferred embodiment, as shown in FIG. 7, an electrical cable 240 connects the connector 340 of the sensor 300 to a connector J5 of the tunable sensor head 200. Thus, the cable 240 carries the electrical vibration signal produced by the transducer 330 to the sensor head 200. Similar to the airborne sensor head 22 described previously, the tunable sensor head 200 preferably includes a cylindrical housing having contact pads 220 at the base of the housing. The contact pads 220 serve to establish electrical connections between the sensor head 200 and the sensor socket 36 in the housing 24.

Figure 9A:
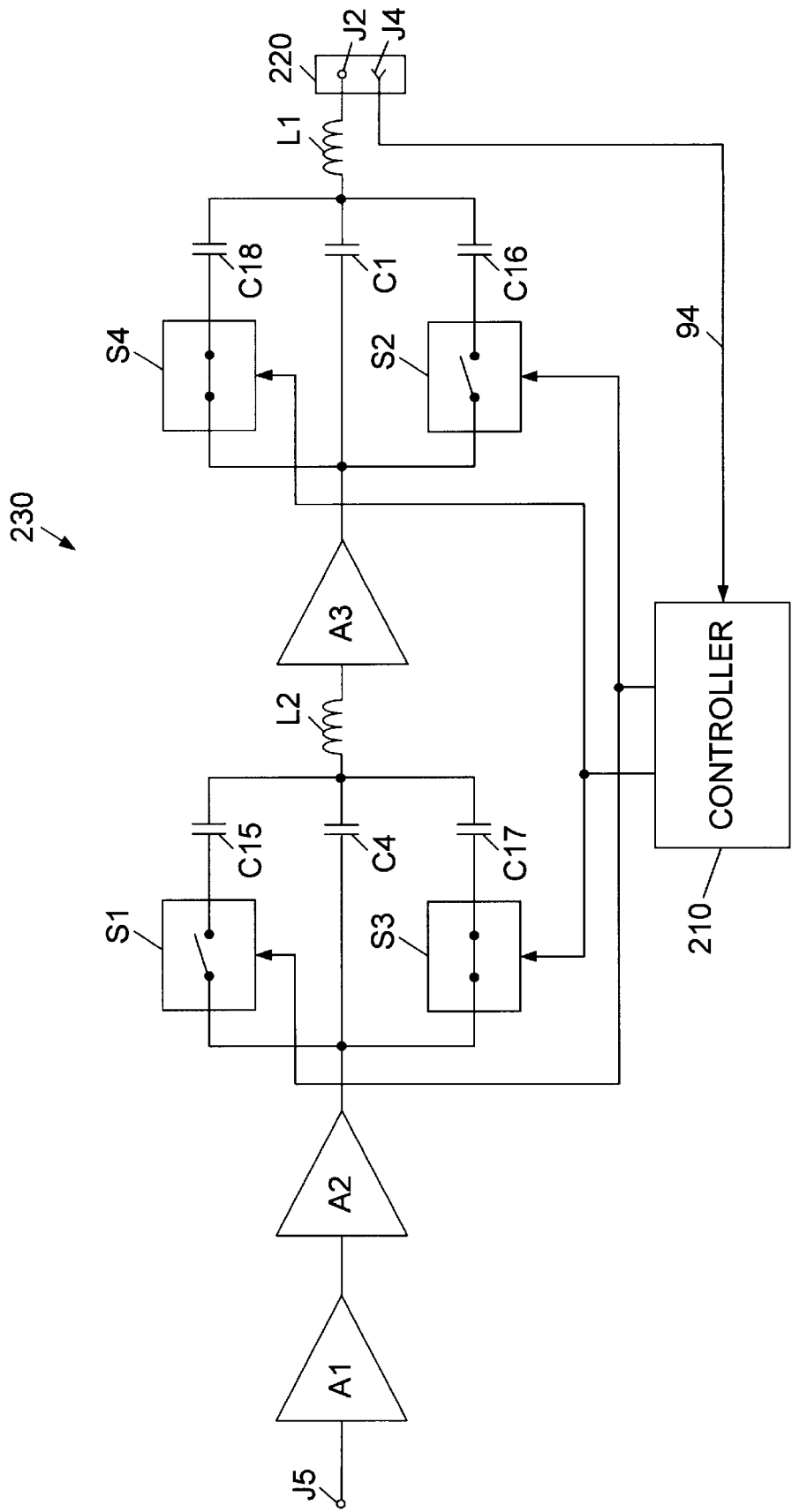
FIG. 9A is a schematic diagram of a tuned circuit for an ultrasonic sensor head, tuned to a 4 kHz frequency band.
Figure 9B:
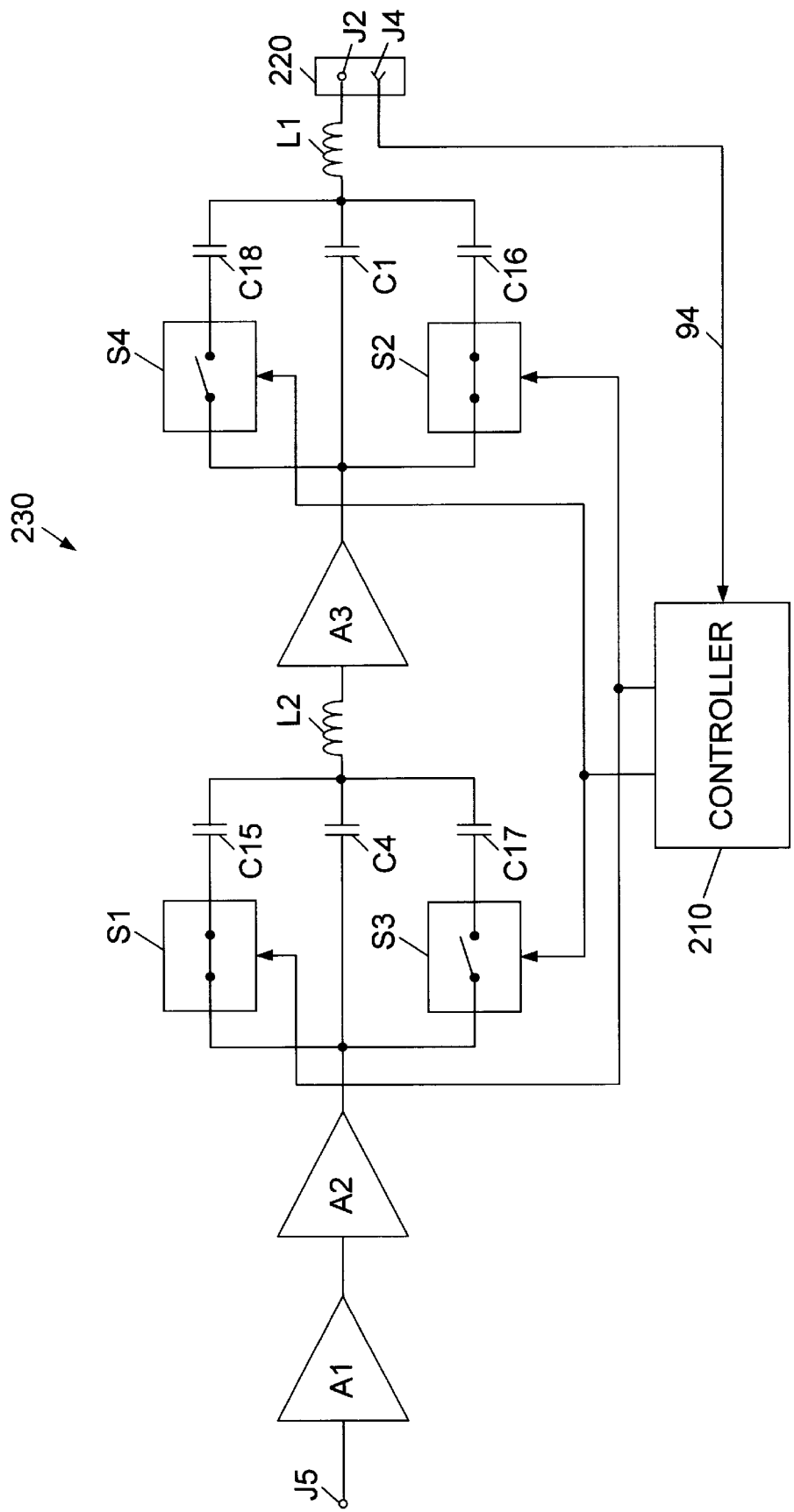
FIG. 9B is a schematic diagram of a tuned circuit for an ultrasonic sensor head, tuned to a 28 kHz frequency band.
Figure 9C:
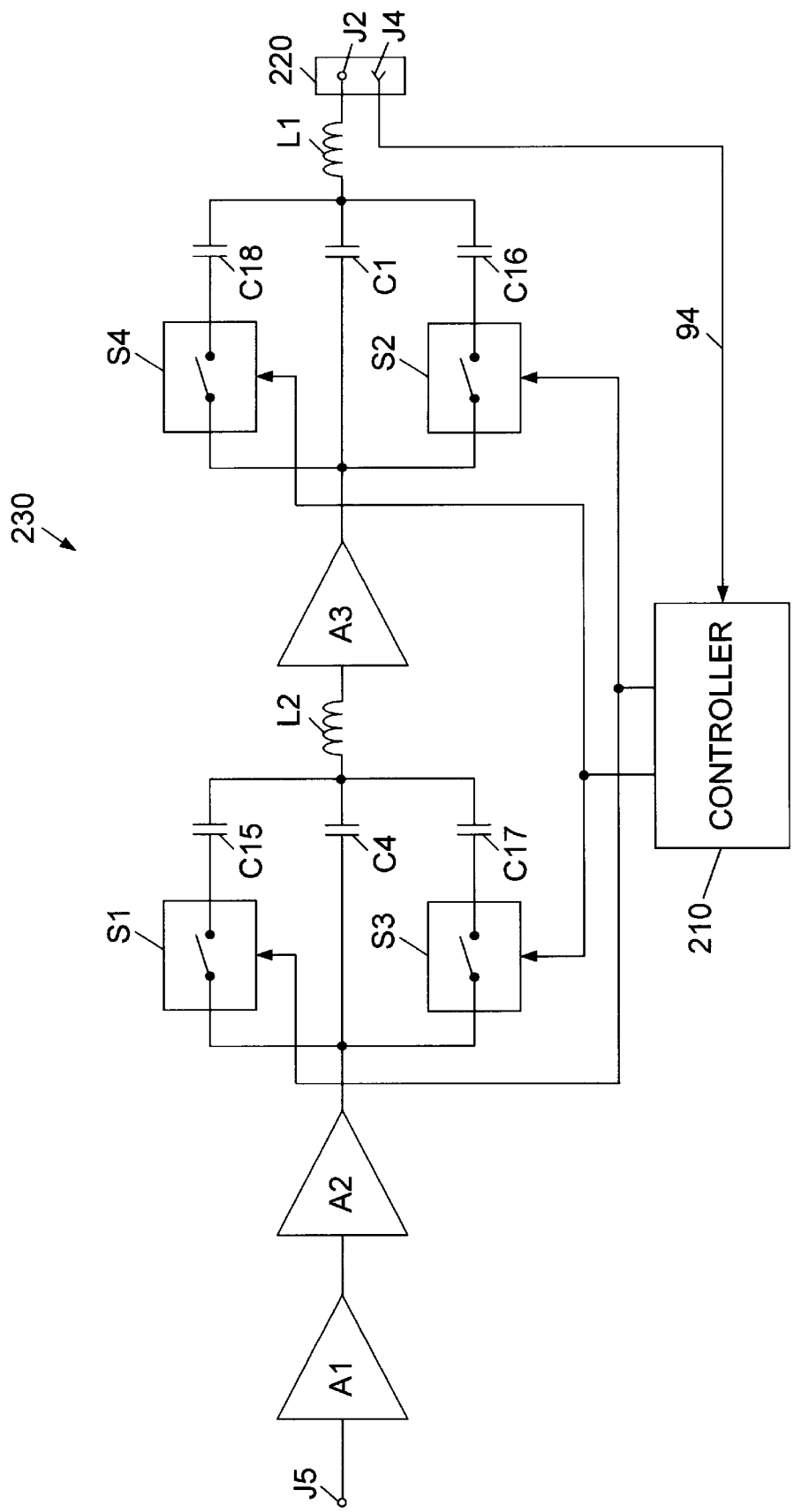
FIG. 9C is a schematic diagram of a tuned circuit for an ultrasonic sensor head, tuned to a 40 kHz frequency band.

FIGS. 9a, 9b, and 9c are schematic representations of a preferred embodiment of a multi-frequency tuning circuit 230 contained within the tunable sensor head 200. Generally, the circuit 230 incorporates two LC tank circuits in series to provide high-Q band-pass tuning of the electrical signal present at the connector J5. As described in greater detail below, the pass band of the LC tank circuits is selectable, as determined by the capacitance value of each of the LC tank circuits.

Referring to FIG. 9a, an electrical vibration signal present at the connector J5 is amplified by preamplifier/buffer A1 and an amplifier A2. With a switch S3 closed, as shown in FIG. 9a, a capacitor C17 is in parallel with a capacitor C4. The parallel capacitors C4 and C17 are in series with an inductor L2, thus forming an LC resonant circuit having a bandpass frequency response. Neglecting series resistance in the circuit, the center frequency of the passband is expressed by:

$$f_o = \frac{1}{2\pi\sqrt{LC}}, \quad (1)$$

where $f_o$ is the center frequency of the filter in Hertz, L is the inductance value of the inductor in Henrys, and C is the capacitance value of the capacitor in Farads. With switch S3 closed and switch S1 open, C in equation (1) is the sum of the capacitance values of C4 and C17. Thus, the amplifier A2, parallel capacitors C4 and C17, and inductor L2 form a first tuned amplifier circuit having a bandpass response centered at $f_o$. Preferably, the values of C4 and C17 are selected to provide a center frequency of approximately 4 kHz.

Similarly, with the switch S4 closed and the switch S2 open, the parallel capacitors C1 and C18 are in series with an inductor L1, thus forming a second LC resonant circuit having a bandpass frequency response. Preferably, the value of C1 is equivalent to the value of C4, and the value of C18 is equivalent to the value of C17. Thus, the amplifier A3, parallel capacitors C1 and C18, and inductor L1 form a second tuned amplifier circuit having a bandpass response also preferably centered at 4 kHz.

Referring now to FIG. 9b, the first and second tuned amplifier circuits are shown with the switches S1–S4 set to provide a different center frequency. In this configuration, switch S1 is closed and switch S3 is open, thus putting the capacitor C15 in parallel with the capacitor C4. Also, switch S2 is closed and switch S4 is open, thus putting the capacitor C16 in parallel with the capacitor C1. Preferably, the values of C16 and C15 are selected to provide a center frequency of approximately 28 kHz when in parallel with C1 and C4, respectively.

With reference to FIG. 9c, the first and second tuned amplifier circuits are shown with the switches S1–S4 set to provide yet a different center frequency. In this configuration, all of the switches S1–S4 are open, such that only the capacitor C4 determines the center frequency of the first tuned amplifier circuit, and only the capacitor C1 determines the center frequency of the second tuned amplifier circuit. Preferably, the values of C1 and C4 are selected to provide a center frequency of approximately 40 kHz for both of the tuned amplifiers. Those skilled in the art will recognize that the values of the capacitors or inductors in the first tuned amplifier circuit could be made somewhat different from the values in the second tuned amplifier circuit. In this manner, "stagger tuning" of the two resonant circuits could be accomplished, thus increasing the bandwidth of the frequency selection.

The state of the switches S1–S4 is determined by a controller 210 which is contained within the sensor head 200. In the preferred embodiment, the controller 210 is a microprocessor manufactured by Microchip Technology, Inc. having a model number PIC16C711-20/SS. Preferably, the switches S1 and S2 are contained within a single latching relay and are controlled by a single control line from the controller 210. Similarly, the switches S3 and S4 are contained within another latching relay, and are controlled by another control line from the controller 210.

Figure 10:
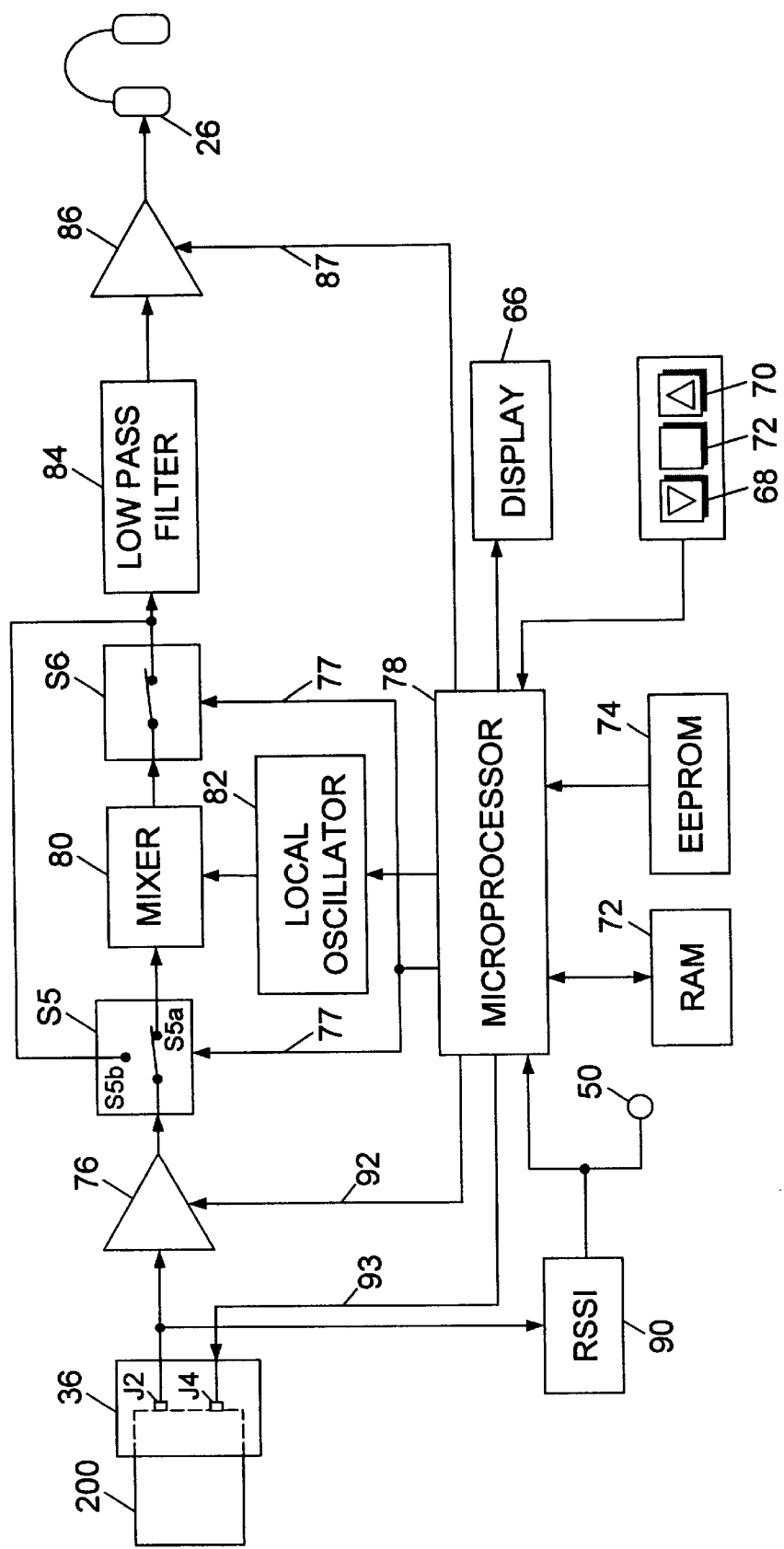
FIG. 10 is a functional block diagram of the ultrasonic monitoring device.

With reference to FIGS. 9a and 10, when the sensor head 200 is plugged into the socket 36 of the housing 24, a serial data line 94 within the sensor head 200 is electrically connected to a serial data line 93. As indicated in FIG. 10, the serial data line 93 is connected to a microprocessor 78 within the housing 24. This connection is made through a contact J4 on the sensor head 200 and a corresponding contact pad 42 within the socket 36. The microprocessor 78, such as a 16-bit Toshiba processor having model number TMP93CS41F, controls the functions of the microprocessor-controlled heterodyne circuit 40 according to firmware instructions and user input.

User input is provided by way of the user-input keys 68, 70, and 72 and the display 66 on the rear face 64 of the housing 24 (see FIG. 6). Using the user-input keys 68, 70, and 72 and display 66, an operator 20 may scroll through a number of options for the frequency band to be monitored during a particular test. In the preferred embodiment, these options include 4, 28, and 40 kHz, as discussed above. When the operator 20 selects the desired frequency band, the microprocessor 78 generates a frequency selection indication on the serial data line 93. This frequency selection indication is carried to the controller 210 in the sensor head 200 by way of the serial data line 94. Based on the frequency selection indication, the controller 210 sets the switches S1–S4 accordingly to tune the sensor head 200 to the desired frequency band.

Alternatively, the desired frequency band may be selected automatically by the microprocessor 78 according to the type of measurement to be performed using the device 10. The types of measurements, which are selectable using the user-input keys 68, 70, and 72 and display 66, may include: "Leak Detection", "Steam Trap", "Mechanical", "Lubrication", "Valve", and "Electrical/Corona." For example, if the operator chooses "Steam Trap" as the measurement application, the microprocessor 78 automatically generates a frequency selection indication on the serial data lines 93 and 94 to cause the controller 210 to set the switches S1–S4 for 40 kHz operation.

The operation of the monitoring device 10 can better be understood by examining a block diagram of the components of the circuit 40 as shown in FIG. 10. Although the embodiment shown in FIG. 10 includes the airborne sensor head 22, it should be understood that the following description is equally applicable to the use of the tuned contact sensor head 104 or the tuned sensor head 200. The sensor head 22 senses the ultrasonic pressure signals 12 and generates a sensor signal, which is an ultrasonic electrical signal based on the ultrasonic pressure signals 12. The sensor head 22 provides the ultrasonic electrical signal to the electrical contacts 42 in the sensor socket 36. The sensor socket 36 provides the ultrasonic electrical signal to a first voltage controlled amplifier 76. As discussed in greater detail hereinafter, the gain of the first voltage controlled amplifier 76 is controlled by the microprocessor 78.

After amplifier 76, the route of the amplified ultrasonic electrical signal is determined by the state of a switch S5. When the switch S5 is as shown in FIG. 10, the ultrasonic electrical signal is routed to a mixer 80. The mixer 80 combines the amplified ultrasonic electrical signal with an oscillator signal provided by a microprocessor-controlled variable frequency local oscillator (LO) 82. At the output of the mixer 80 is a signal consisting of the following components: (1) the amplified ultrasonic electrical signal; (2) the oscillator signal; (3) the sum of the amplified ultrasonic electrical signal and the oscillator signal (sum signal); and (4) the difference between the amplified ultrasonic electrical signal and the oscillator signal (difference signal).

With continued reference to FIG. 10, the path of the signal at the mixer output is determined by the state of a switch S6. When the switch S6 is in the state as shown in FIG. 10, the signal at the mixer output passes through a low pass filter 84 to remove the high frequency components, leaving only the difference signal which is an audio electrical signal within the audible frequency range of a human being. This audio electrical signal is then amplified by a second voltage controlled amplifier 86 that is also controlled by the microprocessor 78. The second voltage controlled amplifier 86 is essentially an audio volume control. Finally, the amplified audio electrical signal is sent to the headphones 26 that generate an audio acoustical signal based on the audio electrical signal.

In the preferred embodiment, the switches S5 and S6 are latching relays controlled by the microprocessor 78 via control lines 77. The purpose of the switches S5 and S6 is to bypass and isolate the mixer 80 when the vibration signal to be monitored is an audio frequency signal. The situations in which this signal falls into the audio range are discussed further below. When this signal is an audio signal, there is no need to mix it with the LO signal. Thus, the mixer is bypassed and the signal is routed directly to the low-pass filter 84 and the amplifier 86.

When the desired frequency band for monitoring is selected, either by choosing a frequency or by choosing a measurement type using the user-input keys 68, 70, and 72 and the display 66, the frequency of the LO signal generated by the LO 82 is automatically adjusted accordingly. For example, when the operator 20 selects a frequency band of 28 kHz, the microprocessor 78 controls the LO to generate an LO signal at approximately 30 kHz. In this situation, the difference signal at the output of the mixer 80 is at about 2 kHz, which is in the audio range.

Alternatively, if the operator 20 suspected that the mechanism being monitored had a lubrication problem, the operator 20 may select "Lubrication" from the list of measurement applications. In this situation, the processor 78 automatically sets the frequency of the LO 82 to approximately 30 kHz so that detected signals in the 28 kHz band, the optimum for detecting lubrication problems, will produce 2 kHz signals at the output of the mixer 80.

The selection of the monitored frequency band also affects the state of the switches S5 and S6. When the selected frequency band is in the audio range, such as 4 kHz, the microprocessor 78 sets the switch S5 to contact S5b and opens the switch S6. This switch state bypasses the mixer 80 so that an audio signal at the output of the amplifier 76 goes directly to the low-pass filter 84. However, if the selected frequency is greater than about 10 kHz, then the microprocessor 78 sets the switches S5 and S6 to the states shown in FIG. 10.

As is true of any amplifier, the amplifiers 76 and 86 each have a maximum amplitude limit. If the amplified signal exceeds the maximum amplitude limit, clipping and distortion of the amplified signal results. As mentioned previously, an amplifier's maximum amplitude limit primarily depends upon the available power supply voltage.

When an ultrasonic electrical signal at the output of any of the sensor heads 22, 104, or 200 is amplified, background noise is amplified as well as the ultrasonic signal that the operator 20 is listening for. If the operator could manually control the gain of the amplifier 76, and inadvertently set the gain too high, a short-duration ultrasonic signal, such as an impact signal, could exceed the maximum amplitude limit of the amplifier 76. If this occurred, the peak of the impact signal would be clipped, since the amplifier 76 cannot produce a signal higher than the limit. In such a situation, the ultrasonic background noise may be amplified so high as to mask the clipped impact signal. If this occurred, it is unlikely that the operator 20 would be able to distinguish the clipped impact signal from the background noise. On the other hand, if the gain of the amplifier 76 is set too low, the impact signal peak may not rise above the noise floor of the amplifier 76.

A preferred embodiment of the present invention overcomes the problems associated with manual gain adjustment by autoranging, or automatically adjusting the gain of the amplifier 76. As explained below, the microprocessor 78 receives a signal indicating the amplitude of the ultrasonic signal at the input to the amplifier 76, and uses this signal to automatically adjust the gain of the amplifier 76. The microprocessor 78 adjusts the amplifier gain to prevent an amplified ultrasonic signal from exceeding the maximum amplitude limit of the amplifier 76.

As shown in FIG. 10, the ultrasonic electrical signal that appears at the input of the amplifier 76 also appears at the input of a received signal strength indicator (RSSI) 90. In the preferred embodiment of the invention, the RSSI 90 is a component of a low-voltage IF receiver, having model number SA637 manufactured by Philips Semiconductor RF Communications Products. At its output, the RSSI 90 produces an envelope waveform of the ultrasonic electrical signal present at its input.

FIG. 11 depicts a preferred embodiment of the RSSI 90. The ultrasonic electrical signal from the sensor head 200 is received by an envelope detector 96. The parallel combination of a capacitor 97 and a resistor 95 provide the envelope detector 96 with a rapid rise and slow decay output. In the preferred embodiment, the values of the capacitor 97 and the resistor 95 are selected to provide the envelope detector 96 with a response time constant of approximately 60 microseconds. This time constant is selected to create an envelope signal that follows the maximum amplitude excursions of the ultrasonic electrical signal. This envelope signal is provided to the microprocessor 78 and to the output jack 50.

While the preferred embodiment uses the envelope detector as shown in FIG. 11, it is expressly understood that the Peak Vue techniques disclosed in U.S. Pat. No. 5,895,857 may be used in accordance with an embodiment of the present invention. Both techniques perform a peak follower function and are able to capture peak amplitude values of short duration ultrasonic signal bursts or rings. Thus, it would be possible to incorporate the Peak Vue method into the present invention.

In the preferred embodiment, when the operator 20 pulls the trigger 54, the microprocessor 78 samples the envelope signal for a period of one second. In this manner, the microprocessor 78 creates a digital representation of the envelope signal consisting of a set of data points, where each data point represents an amplitude level of the envelope signal at a distinct point in time during the one second period. The microprocessor 78 then searches through the set of data points, and finds the peak data point, which is the data point having the maximum amplitude.

Based on the amplitude level of the peak data point, the microprocessor 78 generates a control voltage on the line 92 to set the gain of the amplifier 76. In the preferred embodiment, the microprocessor 78 sets the control voltage to cause the amplifier gain to be such that the signal level at the output of the amplifier 76 is about 85 percent of the amplifier's maximum signal level when a signal having the peak amplitude measured during the one second period is present at the input to the amplifier 76. As long as the trigger 54 remains pressed, the gain of the amplifier 76 stays set at this level. If the operator 20 releases the trigger 54 and then presses it again, the autoranging function as described above is repeated.

Generally, the voltage gain, $G_v$, of an amplifier is expressed as:

$$G_v = \frac{V_o}{V_i}, \qquad (2)$$

where $V_o$ is the amplitude of a voltage signal at the output of the amplifier, and $V_i$ is the amplitude of a voltage signal at the input to the amplifier. In the preferred embodiment of the invention, the microprocessor 78 determines an adjusted voltage gain, $G_{adj1}$, of the amplifier 76 according to:

$$G_{adj1} = \frac{P_1 \times V_{m1}}{V_{peak}}, \qquad (3)$$

where $P_1$ is the predetermined percentage of the maximum voltage signal level, $V_{m1}$, that the amplifier 76 can produce, and $V_{peak}$ is the voltage amplitude of the peak data point. Thus, each time the trigger 54 is pulled, the microprocessor 78 samples the envelope signal for one second and generates a control voltage on the line 92 that adjusts the gain of the amplifier 76 to be equivalent to $G_{adj1}$ as expressed by equation (3).

The value of $V_{m1}$ can vary significantly from one device 10 to another. Therefore, the value of $V_{m1}$ is determined for each device 10 during a calibration test that is performed on each device 10 before the device 10 is used to make measurements. After the value of $V_{m1}$ is determined for a particular device 10, that value is stored in an EEPROM device 74. Subsequently, the microprocessor 78 accesses the value of $V_{m1}$ from the EEPROM device 74 prior to calculating the value of $G_{adj1}$ according to equation (3).

In some situations, the operator 20 may wish to detect pressure or vacuum leaks that produce continuous ultrasonic pressure signals, such as illustrated in FIG. 1. For these situations, the operator 20 can choose to have the device 10 operate in a leak detection mode instead of a mechanical fault detection mode. As explained below, the selected detection mode affects the operation of the autoranging function.

When the operator 20 pulls the trigger 54 while the device 10 is in the leak detection mode, the microprocessor 78 samples the envelope signal from the RSSI 90 for a predetermined period, preferably one second. As discussed previously, the microprocessor 78 then creates a digital representation of the envelope signal consisting of a set of data points, where each data point represents an amplitude level of the envelope signal at a distinct point in time during the one second period. The microprocessor 78 then determines an average amplitude level by summing the amplitudes of all the data points, and dividing the sum by the number of data points.

Based on the average amplitude level, the microprocessor 78 generates a control voltage on the line 92 to set the gain of the amplifier 76. In the preferred embodiment, the microprocessor 78 sets the control voltage to cause the amplifier gain to be such that the signal level at the output of the amplifier 76 is somewhat less than the amplifier's maximum signal level when a signal having the average amplitude measured during the one second period is present at the input to the amplifier 76. As long as the trigger 54 remains pressed, the gain of the amplifier 76 stays set at this level. If the operator 20 releases the trigger 54 and then presses it again, the autoranging function as described above is repeated.

When in the leak detection mode, the microprocessor 78 determines the adjusted voltage gain, $G_{adj1}$ of the amplifier 76 according to:

$$G_{adj1} = \frac{P_1 \times V_{m1}}{V_{avg}}, \quad (4)$$

where $V_{avg}$ is the average voltage amplitude occurring during the predetermined sampling period. Thus, in the leak detection mode, the microprocessor 78 sets the gain of the amplifier 76 based on the average ultrasonic signal level instead of the peak signal level.

Generally, when the amplifier gain is controlled based on the average detected signal level, the gain is set higher than it would be if it were controlled based on the peak level. The higher gain tends to make the continuous ultrasonic signals caused by leaks easier to detect against the noise background. It is possible, though, that high-amplitude transient signals may be clipped when the amplifier gain is set higher. However, since detection of transient signals is not the goal when the device 10 is in leak detection mode, the possibility of clipping these transient signals is generally not of great concern to the operator 20. Should the operator 20 wish to detect the transient signals, the operator 20 may simply set the device 10 to operate in mechanical fault detection mode.

In an alternative embodiment, the microprocessor 78 controls the gain of the audio amplifier 86 based on a control voltage on a line 87. Preferably, the optimum gain setting for the amplifier 86 is determined based in part on the amplitude of the audio signal at the input of the amplifier 86. The amplitude of the audio signal at the input to the amplifier 86 depends on the amplitude of the ultrasonic signal at the input of amplifier 76, the gain of the amplifier 76, and the conversion gain of the mixer 80. Thus the voltage amplitude at the input to amplifier 86, $V_{i2}$, is expressed according to:

$$V_{i2} = V_{i1} \times G_{adj1} \times G_M, \quad (5)$$

where $V_{i1}$ is the voltage amplitude at the input to the amplifier 76, $G_{adj1}$ is the adjusted gain of the amplifier 76 (which could be less than unity), and $G_M$ is the conversion gain of the mixer 80.

The optimum gain setting of the amplifier 86 also depends on the maximum voltage signal level that the amplifier 86 can produce (the clipping level). Since the gain of the amplifier 86 determines the volume level of the sound produced by the headphones 26, the optimum gain of the amplifier 86 also depends on the comfort level of the operator 20. Thus, in the preferred embodiment, the microprocessor 78 determines the gain of the audio amplifier 86 according to:

$$G_{adj2} = \frac{P_2 \times V_{m2}}{V_{i2}}, \quad (6)$$

where $P_2$ is a predetermined percentage of the maximum voltage signal level, $V_{m2}$, of the amplifier 86. Preferably, $P_2$ is 85%. Substituting for $V_{i2}$, the adjusted gain of the audio amplifier 86 is:

$$G_{adj2} = \frac{P_2 \times V_{m2}}{V_{i1} \times G_{adj1} \times G_M}. \quad (7)$$

Equation (7) may also be expressed as:

$$G_{adj2} = \frac{P_2 \times V_{m2}}{P_1 \times V_{m1} \times G_M}, \quad (8)$$

where $P_1$ is the predetermined percentage of the maximum voltage signal level, $V_{m1}$, of the amplifier 76. The values of $G_M$, $V_{m1}$, and $V_{m2}$ are hardware dependent and may vary from one device 10 to another. Therefore, these values are determined during a calibration procedure that is performed on each device 10 before the device 10 is used to make measurements. These values are stored in the EEPROM 74 of each device 10, where the microprocessor 78 accesses them prior to calculating the value of $G_{adj2}$ according to equation (8).

Thus, in the preferred embodiment of the invention, the microprocessor 78 controls the gain of the amplifier 76 according to the detected signal strength of the ultrasonic signal at the input to the amplifier 76, and controls the gain of the amplifier 86 to enhance the audibility of the audio signal. In an alternative embodiment, the microprocessor 78 controls only the gain of the amplifier 76.

It is contemplated, and will be apparent to those skilled in the art from the preceding description and the accompanying drawings that modifications and/or changes may be made in the embodiments of the invention. Accordingly, it is expressly intended that the foregoing description and the accompanying drawings are illustrative of preferred embodiments only, not limiting thereto, and that the true spirit and scope of the present invention be determined by reference to the appended claims.

It will be appreciated that the invention is not limited by the location of the multi-frequency tuning circuit 230 (FIGS. 9a, 9b, 9c). For example, in alternate embodiments, the tuning circuit 230 could be implemented as a component of an airborne sensor head. Further, the circuit 230 could be located within the housing 24, instead of in a separate sensor head. It should be further appreciated that amplifier gain autoranging and frequency selection as described above may be implemented independently in the present invention, and that the magnetically-mounted resonant sensor 300 is not limited to use only in conjunction with the tunable sensor head 200 or the device 10. The resonant sensor 300 could be used in conjunction with other vibration detection equipment, such as the CSI 2120 manufactured by CSI Technology, Inc.

What is claimed is:

1. A device for detecting an emission source of an ultrasonic signal against a background of noise, and for producing an audio signal based upon the ultrasonic signal, where the detecting of the emission source is based at least in part on audibility of the audio signal, and where the ultrasonic signal is a dynamic pressure or vibration signal and has one or more frequency components, the device comprising:

an ultrasonic sensor for sensing the ultrasonic signal during a predetermined sampling period and producing a sensor signal corresponding to the ultrasonic signal;

amplitude characteristic determination means for determining an amplitude characteristic corresponding to the amplitude of the ultrasonic signal during the predetermined sampling period, and for generating an amplitude indication based on the amplitude characteristic;

a signal-conditioning system for receiving the sensor signal and for generating the audio signal based on the sensor signal, the signal-conditioning system including at least one amplifier having adjustable gain for causing the audio signal to have an increased amplitude relative to the sensor signal, said amplifier being capable of producing a predetermined maximum voltage; and automatic gain adjustment means for receiving the amplitude indication and adjusting the gain of the at least one amplifier based at least in part on the amplitude indication and on a predetermined percentage of the maximum voltage of said at least one amplifier to avoid clipping transient signals having increased voltage amplitude relative to said amplitude indication to thereby enhance the audibility of the audio signal.

2. The device of claim 1 wherein the amplitude characteristic determination means are further operable to generate the amplitude indication based on a peak amplitude characteristic corresponding to the ultrasonic signal's maximum amplitude during the predetermined sampling period when the device is operating in a mechanical fault detection mode, and to generate the amplitude indication based on an average amplitude characteristic corresponding to the ultrasonic signal's average amplitude during the predetermined sampling period when the device is operating in a leak detection mode.

3. The device of claim 1 wherein the amplitude characteristic determination means further comprise:

an envelope detector for generating an envelope waveform signal corresponding to the sensor signal; and sampling means for determining discrete data points on the envelope waveform signal, each discrete data point representing an amplitude level of the envelope waveform at a particular time during the sampling period.

4. The device of claim 1 further comprising:

the signal-conditioning system including an ultrasonic amplifier for generating an amplified ultrasonic signal based on the sensor signal, and an audio amplifier for generating an amplified audio signal based on the amplified ultrasonic signal, the ultrasonic amplifier having adjustable ultrasonic gain, and the audio amplifier having adjustable audio gain; and the automatic gain adjustment means for adjusting the gain of at least one of the amplifiers based at least in part on the amplitude indication.

5. The device of claim 1 wherein the ultrasonic sensor further comprises frequency selection means for attenuating a frequency component of the ultrasonic signal having a frequency outside a desired frequency range.

6. The device of claim 1 further comprising electrical frequency selection means including:

frequency switching means for enabling a user of the device to choose one of a plurality of selected frequency components, and for producing a frequency selection indication based upon the selected frequency component; and filter means comprising:
a plurality of filters corresponding to the plurality of selected frequency components, each filter being tuned to one of the selected frequency components and being operable to receive the sensor signal and to electrically attenuate frequencies other than one of the selected frequency components to which the filter is tuned; and filter selection means for receiving the frequency selection indication and selecting one of the filters based on the frequency selection indication.

7. The device of claim 1 further comprising:

a trigger for initiating the predetermined sampling period and for activating the amplitude characteristic determination means to begin sampling the amplitude of the sensor signal; and the amplitude characteristic determination means further for sampling the amplitude of the sensor signal and for generating the amplitude indication based on samples of the amplitude of the sensor signal taken during the predetermined sampling period.

8. A device for sensing a vibration signal against a background of noise, where the vibration signal is produced by a mechanical system and has one or more frequency components, and for producing a sensor signal based on the vibration signal, the device comprising:

a resonant metal rod of a predetermined length related to the resonant frequency, the resonant metal rod for contacting the mechanical system and for vibrating at a resonant frequency within a desired frequency range when the vibration signal has a frequency component within the desired frequency range and when the resonant metal rod is in contact with the mechanical system;

a transducer in contact with the resonant metal rod for producing the sensor signal corresponding to the resonant frequency at which the resonant metal rod is vibrating; and a magnetic annular disc attached to the resonant metal rod adjacent one end thereof, the magnetic annular disc having at the center thereof a circular aperture through which the end of the resonant metal rod penetrates, the magnetic annular disc for contacting the mechanical system and holding the end of the resonant metal rod in contact with the mechanical system by the attractive force of the magnetic annular disc.

9. The device of claim 8 wherein the resonator vibrates at a resonant frequency within the audio frequency range and at a resonant frequency within the ultrasonic frequency range.

10. The device of claim 8 further comprising the resonator for vibrating at a resonant frequency of 4 kHz, 28 kHz, and 40 kHz.

11. The device of claim 8 further comprising:

frequency switching means for enabling a user of the device to choose one of a plurality of selected frequency components, and for producing a frequency selection indication based upon the selected frequency component; and filter means comprising:
a plurality of filters corresponding to the plurality of selected frequency components, each filter being tuned to one of the selected frequency components and being operable to receive the sensor signal and to electrically attenuate frequencies other than one of the selected frequency components to which the filter is tuned; and filter selection means for receiving the frequency selection indication and selecting one of the filters based on the frequency selection indication.

12. The device of claim 8 further comprising:

the resonant metal rod including a metal disc integrally joined to the rod adjacent the one end thereof; and the magnetic annular disc rigidly attached to the metal disc.

13. A device for detecting an emission source of a dynamic signal produced by a mechanical system, where the dynamic signal is a dynamic pressure or vibration signal, the device for producing an audio signal based upon the dynamic signal, where the detecting of the emission source is based at least in part on audibility of the audio signal, the device comprising:

a sensor for sensing the dynamic signal and producing a sensor signal corresponding to the dynamic signal, the sensor signal having one or more frequency components;

electrical frequency selection means for attenuating a frequency component having a frequency outside a desired frequency range, and for passing a selected frequency component having a frequency within the desired frequency range, the electrical frequency selection means comprising:

frequency switching means for enabling a user of the device to choose the selected frequency component, and for producing a frequency selection indication based upon the selected frequency component; and filter means comprising:

a plurality of filters, each operable to receive the sensor signal and to electrically attenuate a frequency component of the sensor signal having a frequency outside the desired frequency range to produce a filtered sensor signal; and filter selection means for receiving the frequency selection indication and selecting one of the filters based on the frequency selection indication;

a signal-conditioning system for receiving the filtered sensor signal and for generating the audio signal based on the filtered sensor signal, the signal-conditioning system comprising:

a local oscillator producing a local oscillator signal;

a heterodyning circuit for mixing the local oscillator signal with the filtered sensor signal to produce the audio signal; and means responsive to said frequency selection indication to set the frequency of the local oscillator signal, whereby the heterodyning circuit produces the audio signal corresponding to the selected frequency component.

14. A device for detecting an emission source of a dynamic signal produced by a mechanical system, where the dynamic signal is a dynamic pressure or vibration signal, the device for producing an audio signal based upon the dynamic signal, where the detecting of the emission source is based at least in part on audibility of the audio signal, the device comprising:

a sensor for sensing the dynamic signal and producing a sensor signal corresponding to the dynamic signal, the sensor signal having one or more frequency components;

electrical frequency selection means for attenuating a frequency component having a frequency outside a desired frequency range, and for passing a selected frequency component having a frequency within the desired frequency range, the electrical frequency selection means comprising:

frequency switching means for enabling a user of the device to choose the selected frequency component, and for producing a frequency selection indication based upon the selected frequency component; and filter means comprising:

a plurality of filters, each operable to receive the sensor signal and to electrically attenuate a frequency component of the sensor signal having a frequency outside the desired frequency range to produce a filtered sensor signal; and filter selection means for receiving the frequency selection indication and selecting one of the filters based on the frequency selection indication, the filter selection means comprising:

a controller for receiving the frequency selection indication and for producing a switching signal based on the frequency selection indication; and switching means having multiple states, the switching means for receiving the switching signal and attaining one of the multiple states based on the switching signal, whereby the state attained by the switching means determines the selection of the filter; and a signal-conditioning system for receiving the filtered sensor signal and for generating the audio signal based on the filtered sensor signal.

15. The device of claim 14 wherein the frequency switching means are further operable to enable the user of the device to choose between selected frequency components of 4 kHz, 28 kHz, and 40 kHz.

16. The device of claim 14 wherein the frequency switching means further comprise:

a user interface for presenting a plurality of frequency component options to the user, and for producing a user input signal based upon the frequency component option selected by the user; and a processor for receiving the user input signal and for producing the frequency selection indication based upon the user input signal.

* * * * *